United States Patent [19]

Winter et al.

[11] Patent Number: 4,942,054

[45] Date of Patent: * Jul. 17, 1990

[54] PROCESS FOR PRODUCING LOW CALORIE FOODS FROM ALKYL GLYCOSIDE FATTY ACID POLYESTERS

[75] Inventors: Daryl B. Winter, Seattle; Richard S. Meyer; Jeffrey M. Root, both of Tacoma; Michael L. Campbell, Kent, all of Wash.

[73] Assignee: Curtice-Burns, Inc., Rochester, N.Y.

[*] Notice: The portion of the term of this patent subsequent to Jun. 20, 2006 has been disclaimed.

[21] Appl. No.: 347,264

[22] Filed: May 3, 1989

Related U.S. Application Data

[63] Continuation-in-part of Ser. No. 122,188, Nov. 18, 1987, Pat. No. 4,840,815, which is a continuation-in-part of Ser. No. 49,625, May 13, 1987, abandoned.

[51] Int. Cl.$^5$ .................................................. A23D 5/00
[52] U.S. Cl. ..................................... 426/611; 426/606; 426/607; 426/804
[58] Field of Search ................. 426/601, 804, 607, 611

[56] References Cited

U.S. PATENT DOCUMENTS

| | | | |
|---|---|---|---|
| 2,759,923 | 8/1956 | Gibbons | 260/210 |
| 2,831,854 | 4/1958 | Tucker et al. | 260/234 |
| 2,893,990 | 7/1959 | Hass et al. | 260/234 |
| 2,931,797 | 4/1960 | Gibbons et al. | 260/210 |
| 3,096,324 | 7/1963 | Goins et al. | 260/234 |
| 3,219,656 | 11/1965 | Boettner | 260/210 |
| 3,248,381 | 4/1966 | Nobile et al. | 260/234 |
| 3,249,600 | 5/1966 | Nobile et al. | 260/234 |
| 3,251,827 | 5/1966 | Schnell et al. | 260/234 |
| 3,347,848 | 10/1967 | Ismail et al. | 260/234 |
| 3,547,828 | 12/1970 | Mansfield et al. | 252/351 |
| 3,558,597 | 1/1971 | von Brachel et al. | 260/234 |
| 3,597,417 | 8/1971 | Myhre | 260/234 |
| 3,598,865 | 8/1971 | Lew | 260/210 R |
| 3,600,186 | 8/1971 | Mattson et al. | 99/1 |
| 3,625,706 | 12/1971 | Myhre | 99/94 |
| 3,634,397 | 1/1972 | Thompson et al. | 260/234 R |
| 3,707,535 | 12/1972 | Lew | 260/210 R |
| 3,714,144 | 1/1973 | Feuge et al. | 260/234 R |
| 3,729,461 | 4/1973 | Pomeranz et al. | 260/210 R |
| 3,772,269 | 11/1973 | Lew | 260/210 R |
| 3,839,318 | 10/1974 | Mansfield | 260/210 R |
| 3,963,699 | 6/1976 | Rizzi et al. | 260/234 R |
| 4,005,195 | 1/1977 | Jandacek | 424/180 |
| 4,349,669 | 9/1982 | Klahr et al. | 536/127 |
| 4,368,213 | 1/1983 | Hollenbach et al. | 426/590 |
| 4,382,924 | 5/1983 | Berling et al. | 424/180 |
| 4,461,782 | 7/1984 | Robbins et al. | 426/549 |
| 4,517,360 | 5/1985 | Volpenhein | 536/119 |
| 4,518,722 | 5/1985 | Volpenhein | 536/119 |
| 4,611,055 | 9/1986 | Yamamoto et al. | 536/119 |
| 4,713,447 | 12/1987 | Letton | 536/186 |
| 4,721,781 | 1/1988 | Rowton | 536/4.1 |
| 4,797,300 | 1/1989 | Jandacek et al. | 426/549 |
| 4,810,516 | 3/1989 | Kong-Chan | 426/548 |
| 4,840,815 | 6/1989 | Meyer et al. | 426/611 |

FOREIGN PATENT DOCUMENTS

| | | |
|---|---|---|
| 0233856 | 2/1987 | European Pat. Off. |
| 0236288 | 2/1987 | European Pat. Off. |
| 156263 | 9/1982 | German Democratic Rep. |

*Primary Examiner*—Donald E. Czaja
*Assistant Examiner*—Euan Federman
*Attorney, Agent, or Firm*—Christensen, O'Connor, Johnson & Kindness

[57] ABSTRACT

Low calorie foods are produced by substituting for the triglyceride fats normally found in foods or food products, a fat substitute comprising an alkyl glycoside fatty acid polyester, the polyester having at least 4 fatty acid ester groups, wherein each fatty acid has from 4 to 24 carbon atoms, and wherein the alkyl glycoside moiety comprises a saccharide portion and an alkyl portion, the alkyl portion having from 1 to 24 carbon atoms.

30 Claims, No Drawings

PROCESS FOR PRODUCING LOW CALORIE FOODS FROM ALKYL GLYCOSIDE FATTY ACID POLYESTERS

CROSS-REFERENCE TO RELATED APPLICATIONS

This is a continuation-in-part of prior application Ser. No. 122,188, filed Nov. 18, 1987, U.S. Pat. No. 4,840,815 which is a continuation-in-part of prior application Ser. No. 049,625, filed May 13, 1987, now abandoned.

TECHNICAL FIELD

This invention relates to a method for producing alkyl glycoside fatty acid polyester fat substitutes and their use thereof in food compositions.

BACKGROUND OF THE INVENTION

One of the most common nutritional problems in the United States today is obesity. In general, obesity results from the consumption of more calories than are expended. Fats contribute from 30% to 40% of the total calories consumed by most Americans. The National Research Council has recommended that total fat intake be reduced to 30% or less of the calories consumed. Consumption of fat is strongly correlated with many disease states, such as heart disease and cancer. Successful reduction of fat consumption has not been achieved because of the dietary habits of the traditional American. Therefore, the search for fat substitutes or low-calorie fats has attracted considerable attention in recent years.

Among the possible low-calorie fats or fat substitutes synthesized to date are: sugar polyesters, sugar alcohol polyesters such as sucrose polyesters (SPE), polyglycerol esters, neopentyl-type alcohol esters, glycerol dialkyl ethers, triglyceride esters of alpha substituted carboxylic acids, diglyceride esters of shortchain dibasic acids, trialkoxytricarballyate, polydextrose, palatinose, polgalactose, N-oil (tapioca dextrin), microbiologically derived products, nonabsorbable synthetic polymers with properties similar to edible oil, tree-derived products, low-metabolized natural fats and oils, biopolymers, branched polysaccharides and jojoba oil. Many of these are reviewed by Hamm, *J. Food Sci.* 49,419 (1984).

Alkyl glycoside compositions are known in the art to be useful as detergents, gelling agents, and as food emulsifiers. Baak, U.S. Pat. No. 3,772,269, discloses a method for making alkyl glycosides by reacting monosaccharides with long chain monohydric alcohols in the presence of an acid catalyst.

Gibbons, U.S. Pat. No. 2,759,923, discloses a method for esterification of glucosides with fatty acids in the presence of an alkaline catalyst. Tetraester alkyl glycosides are produced according to the method of Gibbons at temperaturess above 200° C. and are suitable for use as drying oils in products such as varnishes.

Gibbons et al., U.S. Pat. No. 2,931,797, discloses mixed methyl glucosideglycerol partial esters produced by alcoholysis of triglycerides with methyl glucoside. These partial esters are suitable for use as nonionic emulsifiers.

Myhre, U.S. Pat. No. 3,597,417, discloses a process for preparing fatty acid esters of sugar glycosides, herein incorporated by reference. Myhre first reacts a sugar glycoside with the methyl ester of a short chain acid to produce the sugar glycoside short chain esters. These sugar glycoside short chain esters are then reacted with a long chain fatty acid ester in the presence of an alkali metal alkoxide to produce the sugar glycoside fatty acid ester. Small amounts of these sugar glycoside esters are blended into the shortening component of cake mixes to improve the baking characteristics of the cake mix.

SUMMARY OF THE INVENTION

The present invention provides a process for producing a low calorie food in which the calories derived from fat are reduced. The process consists of substituting, for the normal triglyceride fat ingredients found in foods, a fat substitute comprising an alkyl glycoside fatty acid polyester, the alkyl glycoside fatty acid polyester having at least 4 fatty acid ester groups, wherein each fatty acid has from 4 to 24 carbon atoms, and wherein the alkyl glycoside moiety comprises a saccharide portion and an alkyl portion, the alkyl portion having from 1 to 24 carbon atoms. The fatty acids of the fat substitute are selected from unsaturated fatty acids, saturated fatty acids, and mixtures thereof.

Preferably the saccharide portion of the alkyl glycoside fatty acid polyester is selected from: fructose, glucose, galactose, mannose, ribulose, rhaminose, xylose, xylulose, ribose, arabinose, sorbose, maltose, lactose, cellobiose, melibiose, and 4'-galactosyl lactose. Also, preferably, the alkyl portion of the alkyl glycoside fatty acid polyester is selected from: methyl, ethyl, n-propyl, n-butyl, n-pentyl, n-octyl, n-decyl, n-dodecyl, n-tetradecyl, n-hexadecyl, n-octadecyl and structural isomers thereof. Optionally, the fat substitute may also contain an effective amount of an anti-anal leakage agent to prevent anal leakage. Also, optionally, the fat substitute may be composed of a mixture of two or more alkyl glycoside fatty acid polyesters.

To achieve meaningful calorie reduction in the process of the instant invention, greater than 10% and preferably greater than 33% of the fat ingredients of a food should be substituted with the fat substitute alkyl glycoside fatty acid polyester.

DETAILED DESCRIPTION OF THE INVENTION

In its broadest sense, the present invention is a process for producing a low calorie food using an alkyl glycoside fatty acid polyester as a fat substitute. By employing the fat substitute of the instant invention, not only are low calorie foods produced, but the calories are removed from the fat portion of the diet. The alkyl glycoside fatty acid polyester used in this process has at least 4 fatty acid ester groups, wherein each fatty acid has from 4 to 24 carbon atoms, and wherein the alkyl glycoside moiety comprises a saccharide portion and an alkyl portion, the alkyl portion having from 1 to 24 carbon atoms. The process for producing the low calorie food comprises substituting the alkyl glycoside fatty acid polyester fat substitute for at least a portion of the fat ingredients found in foods which contain fat, especially triglyceride fat, as an important ingredient.

Alkyl Glycoside

The alkyl glycoside starting materials for the present invention include alkyl glycosides of mono-, di-, and trisaccharides. These alkyl glycosides can be produced by procedures well known in the art, or purchased from commercial sources. Methods for producing alkyl glycosides from reducing sugars and monohydric alcohols having from 8 to 25 carbons are described by Lew, U.S. Pat. No. 3,772,269, and Klahr et al., U.S. Pat. No. 4,349,669, both incorporated herein by reference. Examples of suitable reducing saccharides that can be utilized as starting materials for producing alkyl glycosides are monosaccharides such as fructose, glucose, galactose, mannose, ribulose, rhaminose, xylulose, xylose, ribose, and arabinose. A preferred monosaccharide is glucose. Suitable disaccharides for use in conjunction with synthesizing alkyl glycosides include melibiose, lactose, maltose, and cellobiose. The most preferred disaccharide is lactose. Trisaccharides utilized in accordance with the present invention include 4'-galactosyl lactose and reducing trisaccharides of galactose, mannose, glucose, and fructose. The most preferred reducing trisaccharide is 4'-galactosyl lactose. By 4'-galactosyl lactose as used herein is meant O-β-D-galactopyranosyl-(1–4)-O-β-D-galactopyranosyl-(1–4)-D-glucose. These reducing saccharides comprise the saccharide portion of the alkyl glycoside.

Alcohols suitable for forming alkyl glycosides with reducing saccharides include: alkyl, aryl, alkaryl, aralkyl, heteroalkyl, heteroaryl, and monohydric alcohols. The preferred alcohol starting material suitable for production of the alkyl glycosides are alkyl alcohols having from 1 to 24 carbons. The most preferred alcohols are straight chain, fully saturated monohydric alcohols having from 1 to 18 carbons. These include by way of illustration the following alcohols: methyl, ethyl, n-propyl, n-butyl, n-pentyl, n-octyl, n-decyl, n-dodecyl, n-tetradecyl, n-hexadecyl, n-octadecyl and structural isomers thereof (e.g., isopropyl, isobutyl, sec-butyl, tert-butyl, and the like). The very most preferred alcohols are methyl, ethanol and propanol.

In order to be usable in accordance with the method of the present invention, hydroxyl groups on the alkyl glycosides are esterified to form lower acyl ester alkyl glycosides. By lower acyl is meant an acyl group having six or fewer carbon atoms. Preferably, acetyl and propionyl esters are employed. These lower acyl ester alkyl glycosides are formed so that all available hydroxyl groups are converted to esters by conventional methods. An example of a conventional method of esterification that can be employed, is the method of Linstead, R. P.; Rutenberg, A.; Dauben, W. G.; and Evans, W. L. *J. Am. Chem. Soc.*, 62:3260 (1940).

Alkyl Glycoside Fatty Acid Polyesters

After synthesis of the alkyl glycoside lower acyl esters, they are reacted with suitable fatty acid lower alkyl esters to produce the alkyl glycoside fatty acid polyesters of the instant invention.

Suitable fatty acid lower alkyl esters produced for use in conjunction with the method of the present invention are made from saturated and unsaturated fatty acids having from 4 to 24 carbon atoms. Examples of fatty acids usable in accordance with the present invention are butyric, caprylic, capric, lauric, myristic, myristoleic, palmitic, palmitoleic, stearic, oleic, ricinoleic, linoleic, linolenic, oleosteric, arachidic, behenic, erucic, arachidonic and lignoceric. Pure fatty acids or naturally occurring fats and oils can serve as a source of the fatty acid components for alkyl glycoside fatty acid polyesters produced in accordance with the present invention. Suitable fats and oils include coconut oil, palm kernel oil, babassu oils, corn oil, soybean oil, safflower seed oil, peanut oil, olive oil, palm oil, sunflower seed oil, sesame seed oil, rapeseed oil, cotton seed oil, cocoa butter, butterfat, lard, beef tallow, and menhaden oil. Mixtures of fatty acids derived from soybean, safflower, corn, peanut and cotton seed oils are especially preferred because they contain from about 14 to 18 carbon atoms. In general, it is preferred that the fatty acids range from 14 to 18 carbon atoms because they do not volatilize at the interesterification temperatures. To be suitable for use, the fatty acids are converted to lower alkyl fatty acid esters by conventional esterification procedures prior to reacting with a suitable alkyl glycoside lower alkyl ester. Examples of suitable lower alkyl fatty acid esters include, but are not limited to: myristate fatty acid methyl ester (FAME), palmitate FAME, palmitoleate FAME, stearate FAME, oleate FAME, linoleate FAME, myristate fatty acid ethyl ester (FAEE) palmitate FAEE, palmitoleate FAEE, stearate FAEE, oleate FAEE, and linoleate FAEE.

Prior to combining the reactants, both the lower alkyl fatty acid ester and the alkyl glycoside lower alkyl ester are thoroughly dried by conventional procedures, for example, vacuum drying over anhydrous sodium or magnesium sulfate, followed by dry nitrogen purging. The substantially anhydrous lower alkyl fatty acid ester and alkyl glycoside lower alkyl ester are combined in mole ratios of at least 4:1, and preferably from 6:1 to 15:1, depending on the alkyl glycoside lower alkyl ester. To achieve high yields in accordance with the present invention, a catalyst is combined with the reactants prior to heating. Suitable catalysts include the alkali metal catalysts. Sodium and potassium are the most preferred of the alkali metals. Catalysts can be used in amounts up to 5% by weight but are preferably used in amounts on the order of 2% by weight.

As mentioned above, in order to achieve the high yields possible in accordance with the present invention, all components of the reaction mixture must be combined at room or slightly elevated temperature. It is preferred that the reaction mixture be heated to a reaction temperature gradually, preferably a heating rate no greater than 3° C. per minute. Preferably reaction temperatures range from 100° C. to 125° C., while the temperature range of 105° C. to 115° C. is most preferred. During the heating and maintenance of the reaction temperature, the area over the reaction vessel is evacuated and flooded with a dry, inert atmosphere. The inert atmosphere can comprise any inert gas, but nitrogen is preferred because of its cost and availability. In order to obtain the yields established in accordance with the present invention, the vacuum pulled over the reaction mixture must be less than 15 torr and, preferably, in the range of from 0 to 8 torr. Under these conditions, a 95% to 99% yield can be achieved while maintaining the reaction mixture of the reaction temperature for only about two to two and one-half hours.

Exemplary alkyl glycoside fatty acid polyesters produced in accordance with the present invention include: methyl glucoside tetraoleate, ethyl glucoside tetraoleate, the ethyl glucoside fatty acid polyester made from peanut oil FAME, methyl glucoside fatty acid polyester made from a 50:50 blend of peanut oil FAME and methyl stearate, ethyl galactoside fatty acid polyester made from peanut oil FAEE, n-octyl glucoside fatty acid polyester made from peanut oil FAME, ethyl lactoside fatty acid polyester made from peanut oil FAME, and ethyl 4'-galactosyl lactoside fatty acid polyester.

By alkyl glycoside fatty acid polyesters as used in this invention is meant alkyl glycosides in which four or more of the alkyl glycoside hydroxyl groups have been esterified with a fatty acid. Yields reported for alkyl glycoside fatty acid polyesters in this invention are based on $n-1$ or more alkyl glycoside hydroxyl groups being esterified with a fatty acid, where n is the maximum number of ester bonds possible for a given alkyl glycoside.

Both homogeneous (simple) and heterogeneous (mixed) alkyl glycoside fatty acid polyesters can be produced in accordance with the method of this invention. Examples of preferred homogeneous alkyl glycoside fatty acid polyesters are: methyl glucoside tetraoleate, ethyl glucoside tetraoleate, ethyl galactoside tetrapalmitate, and ethyl lactoside heptastearate. Heterogeneous alkyl glycoside fatty acid polyesters, in which two or more different fatty acid moieties are esterified to one alkyl glycoside molecule, are produced by blending two or more fatty acid lower alkyl fatty acid esters in the reaction mixtures in predetermined ratios. For example, ethyl lactoside heptaacetate, ethyl oleate and ethyl palmitate can be added to the reaction mixture in a ratio of 1:6:4 to produce a heteropolyester of ethyl lactoside. Alternatively, alkyl glycoside lower acyl esters can be reacted with heterogeneous mixtures of fatty acid lower alkyl esters produced from natural oils such as peanut oil to produce heterogeneous alkyl glycoside fatty acid polyesters. An example of such a compound is ethyl 4'-galactosyl lactoside fatty acid polyester made from peanut oil FAME.

Alkyl Glycoside Fatty Acid Polyester Fat Substitute

Alkyl glycoside fatty acid polyesters produced by the above procedures are suitable for use as fat substitutes. Preferred fat substitute food compositions are composed of both nonfat ingredients and fat ingredients wherein from about 5% to about 95% of the total fat ingredients are the alkyl glycoside fatty acid polyesters of the present invention in which alkyl glycoside is esterified to at least four fatty acids. The alkyl glycoside portion of the alkyl glycoside fatty acid polyester fat substitute is preferably the reaction product of a reducing mono-, di-and trisaccharide with a monohydric alcohol having from 1 to 24 carbons. The preferred alkyl glycoside portions are the reaction product of glucose, galactose, lactose and maltose with ethanol and propanol. The fatty acid portion of the alkyl glycoside fatty acid polyester fat substitute food composition is a fatty acid having from 4 to 24 carbons. Preferred fatty acids have from 12 to 18 carbons.

It has been discovered that by blending saturated and unsaturated lower alkyl fatty acid esters in the reaction mixture, heterogeneous alkyl glycoside fatty acid polyesters can be produced which do not exhibit undesired anal leakage of the type described below. At least 25% of the lower alkyl fatty acid esters in the reaction mixture must be derived from saturated fatty acids having 12 or more carbons in order to produce a heterogeneous alkyl glycoside fatty acid polyester which does not exhibit anal leakage. It is believed that a substantial portion of the alkyl glycoside molecules contain both saturated and unsaturated fatty acids in the final product. These alkyl glycoside fatty acid polyesters are to be distinguished from the mixed high melting and low melting point alkyl glycoside fatty acid polyester compounds described below.

An alternative alkyl glycoside fatty acid polyester composition suitable for use as a fat substitute food composition is a mixture of low melting point and high melting point alkyl glycoside fatty acid polyesters. Examples of preferred fatty acids suitable for producing low melting point alkyl glycoside fatty acid polyester compounds are C14 to C18 unsaturated fatty acids. Equivalent low melting point compounds are produced from sources that produce mixtures of saturated and unsaturated fatty acids. Nonlimiting examples of such compounds are ethyl glucoside fatty acid polyesters from peanut oil FAME. By low melting point alkyl glycoside fatty acid polyester as used herein is meant those alkyl glycoside fatty acid polyesters which are liquid at room temperature.

Preferred high melting point alkyl glycoside fatty acid polyester compounds of the present invention are composed of fatty acid esters in which the fatty acid moiety is a saturated fatty acid having from 12 to 18 carbons. Examples of preferred high melting point alkyl glycoside fatty acid polyester compounds are: methyl glucoside tetralaurate, ethyl glucoside tetrapalmitate, ethyl galactoside tetrapalmitate and ethyl glucoside tetrastearate. By high melting point alkyl glycoside fatty acid polyester as used herein is meant those alkyl glycoside fatty acid polyesters which are solid at temperatures above 37° C.

Alkyl Glycoside Fatty Acid Polyester AAL Agent

It has been discovered that alkyl glycoside fatty acid polyesters that have a melting point of about 37° C. or higher can act as anti-anal leakage (AAL) agents of the type described by Jandacek, U.S. Pat. No. 4,005,195, and Robbins et al., U.S. Pat. No. 4,461,782. Accordingly, an effective amount of these glycoside AAL agents can be blended with low melting point alkyl glycoside fatty acid polyesters to produce fat substitute food compositions which are oils at ambient temperature but which do not exhibit the undesirable anal leakage side effect observed when homogeneous low melting point glycoside fatty acid polyesters are used as low calorie fat substitutes alone. Suitable alkyl glycoside fatty acid polyester AAL agents are produced by interesterification of lower acyl ester glycosides with lower alkyl fatty acid esters wherein the fatty acid moiety of the lower alkyl fatty acid ester is a saturated fatty acid having from 14 to 18 carbon atoms. Preferred saturated fatty acids are palmitic and stearic acid. Equivalent glycoside AAL agents are produced by the interesterification of lower alkyl fatty acid esters with blends of lower alkyl fatty acid esters wherein the fatty acid moiety is predominantly saturated with lesser amounts of unsaturated fatty acids. The critical property of the resultant glycoside AAL agent being only that it have a melting point higher than 37° C.

Examples of low calorie fat substitute food compositions of the present invention which do not cause undesired anal leakage side effects are provided in Table I below.

TABLE I

| Low Melting Point Alkyl Glycoside Fatty Acid Polyester | High Melting Alkyl Glycoside Fatty Acid Polyester AAL Agent |
|---|---|
| Ethyl glucoside tetraoleate | Ethyl glucoside tetrapalmitate |
| Ethyl galactoside fatty acid polyester of peanut oil FAME | Ethyl galactoside tetrapalmitate |
| Ethyl 4'-galactosyl lactoside | Ethyl 4'-galactosyl lactoside |

TABLE I-continued

| Low Melting Point Alkyl Glycoside Fatty Acid Polyester | High Melting Alkyl Glycoside Fatty Acid Polyester AAL Agent |
| --- | --- |
| fatty acid polyester | decapalmitate |
| n-octylglucoside fatty acid polyester of peanut oil FAME | n-octylglucoside tetrastearate |
| Ethyl glucoside fatty acid polyester of peanut oil FAME | Ethyl glucoside tetrastearate |
| Ethyl lactoside fatty acid polyester of peanut oil FAME | Ethyl lactoside octastearate |

The amount of alkyl glycoside fatty acid polyester AAL agent to be blended with the low melting point glycoside fatty acid polyester, is known to those skilled in the art and depends upon the amount of low calorie fat substitute composition consumed. It is preferred, that from about 5% to about 50% of the fat ingredients in the fat substitute food composition consist essentially of a high melting point alkyl glycoside fatty acid polyester.

Process for Producing Low Calorie Foods

Low calorie foods are produced in accordance with the present invention by preparing foods according to art standard recipes and procedures, with the substitution of the alkyl glycoside fatty acid polyester fat substitute for at least a portion of the triglyceride fat ingredients normally found in foods. The instant fat substitute is particularly well suited for replacing the triglyceride fat ingredients in foods containing "visible fats" such as: shortenings, margarines, butter, salad and cooking oils, mayonnaise, salad dressing, confectioners' coatings, and the like. The instant fat substitute is also suitable for replacing the fat ingredients in foods containing "invisible fats", such as oilseeds, nuts, dairy products, and animal products. By the term "visible fat", as used herein, it is meant fats and oils that have been isolated from animal tissues, oilseeds, or vegetable sources and are used or added to produce the food products described above. The term "invisible fat" is used herein to mean fats and oils that have not been or are not isolated from animal or vegetable sources, and are consumed along with the protein and carbohydrate constituents of these sources as they are naturally constituted. Fat ingredients normally found in foods containing either "visible fats" or "invisible fats" are predominantly triglycerides, with minor amounts of mono- and diglycerides, free fatty acids, phosphatides, sterols, fatty alcohols, tocopherols, carotenoids, and certain vitamins.

To prepare a low calorie food from one having "invisible fat" ingredients generally requires the removal of a portion of the "invisible fat" ingredients, followed by addition of an equal, greater, or lesser amount of the alkyl glycoside fatty acid polyester fat substitute. By way of example, a low calorie spreadable peanut product that is nutritionally equivalent to peanut butter (i.e., has the same protein quantity and quality), but without as many calories, can be prepared by removing a portion of the peanut oil from the peanut butter and replacing it with an alkyl glycoside fatty acid polyester (preferably prepared from peanut oil FAME). Removing the endogenous peanut oil can be achieved by merely decanting the oil from unstabilized peanut butter, or by simple oil extraction.

Foods having "visible fat" ingredients are ones in which a triglyceride fat or oil is usually added to other ingredients to prepare the food product. To prepare a low calorie food from one having "visible fat" ingredients, at least a portion of the added triglyceride fat or oil ingredients are replaced with the alkyl glycoside fatty acid fat substitute of the present invention.

According to the instant invention a low calorie food, containing nonfat ingredients and fat ingredients, either "visible" or "invisible", is prepared by substituting for the fat ingredients a fat substitute comprising an alkyl glycoside fatty acid polyester, as defined above. By the term substituting, as used herein, it is meant either simply replacing exogenously added triglyceride fat ingredients, or removing endogenous fat ingredients, from food, followed by addition of an equal, greater or lesser amount of the alkyl glycoside fatty acid polyester.

The fatty acid ester moiety of the alkyl glycoside fatty acid polyester fat substitute may be selected from among saturated fatty acids, unsaturated fatty acids and mixtures thereof. However, it is preferred, for most uses, that the fatty acid ester groups be selected from the group consisting of unsaturated fatty acids, and mixtures of saturated and unsaturated fatty acids having from 4 to 24 carbon atoms. The terms saturated and unsaturated fatty acids are used herein in their normal sense, regardless of how they are formed (i.e. hydrogenation or partial hydrogenation). Included in the term unsaturated is monounsaturated (mono enoic) and polyunsaturated (poly-enoic), as well as specific positional isomers.

In order to achieve highly desirable organoleptic properties, it is most preferred that the composition of the fatty acid in the alkyl glycoside fatty acid polyester be the same or equivalent to the composition of fatty acids in the triglycerides they replace. By way of example, most preferred fatty acid ester groups in an alkyl glycoside fatty acid polyester used to replace peanut oil in a low calorie spreadable peanut product would be peanut oil fatty acid ester groups. Similarly, a low calorie Italian salad dressing normally containing safflower oil as the fat ingredient would be prepared by replacing at least a portion of the safflower oil with an alkyl glycoside fatty acid polyester made from safflower oil FAME. Tables describing the composition of fatty acids in typical triglyceride vegetable oils and animal fats are readily available (see for example Table VII p. 21 in *Food Fats and Oils*, Institute of Shortening and Edible Oils, Inc., 1750 New York Avenue N.W., Washington, D.C.).

The amount of alky glycoside fatty acid polyester to be substituted for the fat ingredients in a low calorie food product depends on the application. In most cases, greater than 10% of the fat ingredients are replaced with the alkyl glycoside fatty acid polyester to achieve meaningful calorie reduction. Up to 100% of the fat ingredients of a food can be substituted with the alkyl glycoside fatty acid polyester of the present invention. However, it is recognized that fat ingredients provide many essential nutrients in human and animal diets. For example, fat ingredients in foods provide fatty acids, which are precursors of the prostaglandins as well as being carriers for fat soluble vitamins. It is therefore preferred that less than 100% of the fat ingredients be replaced by the fat substitute of the instant invention in any one food product. Accordingly, it is preferred that from 25%-85% of the fat ingredients in a food be replaced with an alkyl glycoside fatty acid polyester fat substitute, while it is most preferred that from 33%-75% be replaced with this fat substitute.

The alkyl glycoside fatty acid polyester fat substitute may be composed of a single homogeneous (saturated or unsaturated) or heterogeneous (saturated or unsaturated) alkyl glycoside fatty acid molecular species, or may be a mixture of two or more molecular species. By way of illustration, a fat substitute composed of a mixture of alkyl glycoside fatty acid polyesters is prepared by mixing two or more alkyl glycoside fatty acid polyesters in which the fatty acid moieties are selected from among: homogeneous saturated, homogeneous unsaturated, heterogeneous saturated, heterogeneous unsaturated, and a mixture of heterogeneous saturated and unsaturated. For example, a low calorie food prepared by substituting for the fat ingredients a mixture of alkyl glycoside fatty acid polyesters, in which the fatty acids are unsaturated fatty acids, would be a mixture of methyl glucoside tetraoleate and ethyl galactoside tetrapalmitate, or a mixture of methyl glucoside dioleate-dilinoleate and methyl glucoside dicaproleate-dilauroleate. Similarly, an example of a mixture of alkyl glycoside fatty acid polyesters, in which the fatty acids are selected from saturated and unsaturated fatty acids, would be methyl glucoside tetrapalmitate and ethyl galactoside tetraoleate, or methyl glucoside polyester, prepared from corn oil FAME, and ethyl galactoside polyester prepared from rapeseed oil.

Optionally, the fat substitute may include an anti-anal leakage agent (AAL) of the type described by Jandacek, U.S. Pat. No. 4,005,195, herein incorporated by reference. Exemplary anti-anal leakage agents include fatty acids having melt points above 37° C. and sources thereof: i.e., mono-, di-and triglycerides; nonreducing di- and trisaccharide polyesters having $C_{10}$-$C_{22}$ saturated fatty acid ester groups; and alkyl glycoside fatty acid polyesters having melt points above 37° C. Also, optionally, the fat substitute of this invention may include essential fat nutrients (e.g. 20-carbon, polyunsaturated fatty acids especially arachidonic acid) and fat soluble vitamins.

In most cases, it is unnecessary to add anti-anal leakage agents to the fat substitute of the instant invention. This is especially the case when the diet is a normal one and includes foods containing "invisible fats", such as dairy products, eggs, meat, poultry, fish, fruits, vegetables, legumes, nuts, soy, grains and the like. "Invisible fats" found in animal tissues, oilseeds, or vegetable sources are consumed as a normal part of the diet, and are known to comprise 57% of the fat available for consumption in the normal U.S. diet. A portion of these "invisible fats" are triglyceride sources of fatty acids, having melt points above 37° C. (i.e. AAL agents), and therefore it is unnecessary to include any other AAL agents in the fat substitute. Accordingly, alkyl glycoside fatty acid polyesters containing all unsaturated fatty acid ester groups are especially useful as fat substitutes in replacing triglyceride fats and oils in food products containing "visible fats".

The alkyl glycoside fatty acid polyester fat substitutes of the present invention are also useful for cooking foods (i.e. frying, basting, coating, etc.). In this respect, use of the instant fat substitute does not depart from normal cooking procedures (see for example *Joy of Cooking* by Irma Rombauer and Marion Rombauer-Becker), except that nominal triglyceride fats and oils are replaced in part or in total with an alkyl glycoside fatty acid polyester. By way of illustration, a low calorie fried food product is produced by heating a fat substitute comprising an alkyl glycoside fatty acid polyester as defined above, and thereafter contacting a food with the heated fat substitute for a time effective to produce a low calorie fried food product. Similarly, low calorie foods may be produced by simply contacting a food with the alkyl glycoside of the instant invention, as for example in basting foods. One of ordinary skill will appreciate the many other uses of the instant fat substitute in preparing low calorie and low fat foods.

The following examples are intended to be illustrative of the present invention and to teach one of ordinary skill how to make and use the invention. These examples are not intended in any way to limit the invention or otherwise limit the protection afforded by Letters Patent hereon.

PREPARATION OF ALKYLGLYCOSIDE POLYESTERS

EXAMPLE I

Ethyl glucoside tetraacetate

In a 1000 ml three-necked flask equipped with an efficient stirrer and a thermometer, 400 ml acetic anhydride is cooled in an ice and $H_2O$ mixture. 20 mls of conc. $H_2SO_4$ is added to the mixture dropwise. The solution is cooled to below 20° C. and 100.0 g of anhydrous D-glucose is added to the stirred mixture, over a ½ hour period. The reaction temperature is maintained between 30° C. and 40° C. Red phosphorus (30 g) is added after cooling the mixture to 20° C., followed by the addition of 180 g bromine (58 ml) at a rate sufficient to keep the reaction temperature below 20° C. Water (3.6 ml) is added dropwise to the continuously stirred and cooled mixture over about a ½ hour period to prevent the temperature from rising over 20° C. The reaction mixture is kept at room temperature for 2 hours. Methylene chloride (300 ml) is then added, and the mixture is filtered through fine glass wool. The reaction flask and filter funnel are washed with 50 ml $CH_2Cl_2$. The filtrate is poured into water (near 0° C.) contained in a separatory funnel. After washing, the $CH_2Cl_2$ layer is drawn off into another separatory funnel into 0° C. water. The operation is repeated by adding 50 ml $CH_2Cl_2$ to the original aqueous mixture and combining the $CH_2Cl_2$ extracts. After vigorous shaking, the $CH_2Cl_2$ layer is poured into 50 mls of a stirred saturated aqueous solution of sodium hydrogen carbonate pH 6.0. The $CH_2Cl_2$ layer is then dried with $NaSO_4$, and the mixture is filtered. The product, acetyl bromoglucose, is recrystallized twice from diethyl ether. The crystalline mass is then admixed with ethanol in the presence of an equimolar amount of $Ag_2CO_3$ and maintained at a temperature of 30°-40° C. for 16 hours, with vigorous mixing in the dark. The crude ethyl glucoside tetraacetate is crystallized twice from ethanol as described above, to produce substantially pure ethyl glucoside tetraacetate.

EXAMPLE II

Ethyl galactoside tetraacetate

D-galactose is substituted for D-glucose in the reaction mixture described in Example I. Ethyl galactoside tetraacetate is recrystallized from methylene chloride.

EXAMPLE III

4'-Galactosyl lactose

4'-galactosyl lactose is prepared by adding 1200 g lactose to a 10 liter jar fermentor containing 6 liters of a *Cryptococcus laurentii* broth containing neopepetone (10 g/l) and dextrose (20 g/l) at pH 5.6. The broth containing lactose is incubated at 25°–30° C. for 6 hrs, after which it is centrifuged to remove the microorganisms. The eluate is chromatographed on an activated carbon column, concentrated, filtered and the 4'-galactosyl lactose is crystallized from ethanol.

EXAMPLE IV

Ethyl 4'-galactosyl lactoside decaacetate 30 g of 4'-galactosyl lactose produced as described in Example III is substituted for the D-glucose in the reaction mixture described in Example I. Crude ethyl 4'-galactosyl lactose decaacetate is recrystalized from $CH_2Cl_2$ as described above.

EXAMPLE V

Ethyl 4'-galactosyl lactose polyoleate

Methyl oleate (51 g, 0.1720 mole) is placed in a three-necked, round-bottomed flask equipped with a magnetic stirrer, stopcocks, a vacuum take-off line leading to a liquid nitrogen cold trap, manometer, two condensers, thermometers, a vacuum pump and purged with dry $N_2$ gas for 30 min. Ethyl 4'-galactosyl lactose decaacetate (15 g, 0.0155 mole) is added and the $N_2$ purging is continued for an additional 15 min. The mole ratio of methyl oleate to ethyl 4'-galactosyl lactose decaacetate is 11:1. Sodium metal (2% of the reactants by weight, 1.3 g) is added. Heating is started with continuous stirring under dry nitrogen atmosphere. The reaction mixture is heated to 110° C. to 115° C. and pressure is maintained at 0 to 8 mm torr. Synthesis of alkyl glycoside polyesters requires constant dispersion of liquid sodium, liquid ethyl 4'-galactosyl lactose decaacetate and liquid fatty acid methyl esters for optimal interesterification under $N_2$ gas. Interesterification is assumed to begin when catalytic sodium metal and ethyl 4'-galactosyl lactose decaacetate melts and the reaction mixture becomes homogeneous. Interesterification is continued under constant conditions for two and one-half hours. Volatile methyl acetate is condensed on a liquid nitrogen Dewer column to drive the reaction towards ethyl 4'-galactosyl lactose esterification. Ethyl 4'-galactosyl lactose polyoleate is purified by a modification of the method of Hamm, *J. Food Sci.* 49:419 (1984). The crude ethyl 4'-galactosyl lactose polyoleate reaction mixture is neutralized with sufficient acid, dissolved in hexane, stirred and bleached with activated charcoal. The reaction mixture is then filtered with Whatman No. 4 filter paper to remove charcoal particles, and the filtrate is washed with 6×400 ml aliquots of methanol allowing enough time for separation. The more dense methanol insoluble layer containing ethyl 4'-galactosyl lactose polyoleate is separated, dried over anhydrous sodium sulfate and filtered with Whatman No. 4 filter paper. Methanol and hexane are then evaporated from ethyl 4'-galactosyl lactose polyoleate. The color of the polyester is golden yellow, similar to corn oil.

EXAMPLE VI

Ethyl 4'-galactosyl lactose polyester from soybean oil FAME

The procedure of Example V is repeated substituting 63.26 g of soybean oil FAME for methyl oleate. The average molecular weight of soybean FAME is assumed to be about 278.01. Ethyl 4'-galactosyl lactose decaacetate (20 g, 0.0207 mole) is added to the soybean FAME. An ethyl 4'-galactosyl lactose polyester of soybean oil is produced.

EXAMPLE VII

Ethyl 4'-galactosyl lactose polyester from safflower oil FAME and methyl stearate The procedure of Example V is repeated by combining methyl stearate (8.04 g), safflower oil FAME (32.16 g), ethyl 4'-galactosyl lactose decaacetate (12.00 g) and 2% by weight Na (1.04 g). An ethyl 4'-galactosyl lactose polyester of 80:20 (w/w) blend of safflower oil FAME and methyl stearate is produced.

EXAMPLE VIII

Ethyl lactoside polyester from safflower oil FAME and methyl stearate

Substantially anhydrous methyl stearate (4.34 g), safflower oil fatty acid methyl ester (FAME) (39.06 g), and ethyl lactoside heptaacetate (12.5 g) are mixed with 2% by weight Na (1.12 g), based on the weight of the reactants. Interesterification is carried out under dry $N_2$ atmosphere by first gradually heating the reaction mixture to a temperature in the range of 105° C. to 110° C. and maintaining that temperature for two hours. The pressure over the reaction vessel is maintained at 0 to 5 torr. The mole ratio of the fatty acid methyl esters to ethyl lactoside heptaacetate is 7:1. An ethyl lactoside fatty acid polyester of 90:10 (w/w) blend of safflower oil FAME and methyl stearate is produced. The crude methyl lactoside fatty acid polyester is purified as described in Example V.

The foregoing procedure is repeated, except the safflower oil FAME and methyl stearate blend is replaced by an equivalent amount of safflower oil FAME alone. Ethyl lactoside fatty acid polyester of safflower oil FAME is produced.

EXAMPLE IX

Ethyl lactoside polyester from soybean oil FAME

Substantially anhydrous soybean oil FAME (0.2947 mole) and ethyl lactoside heptaacetate (0.0368 mole) are mixed with 2% by weight sodium metal (2.1 g). The mole ratio of soybean oil FAME to ethyl lactoside heptaacetate is 7:1. Interesterification is performed under dry $N_2$ atmosphere at 115° C. to 118° C. for three hours. The pressure is maintained at 0 to 5 torr. Purification of the crude ethyl lactoside polyester is performed essentially as described in Example V.

EXAMPLE X

Ethyl maltoside polyoleate

Substantially anhydrous methyl oleate 97% pure (69.9 g, 0.2358 mole) and ethyl maltoside heptaacetate (20 g, 0.0294 mole) and 2% Na (1.8 g) are mixed. Interesterification is carried out at 105° C. to 110° C. for two and one-half hours under the conditions set forth in Example V. The final mole ratio of methyl oleate to ethyl maltoside heptaacetate is 7:1.

EXAMPLE XI

Ethyl lactoside, glucoside, and galactoside polyoleate 20 g of D-lactose is substituted for the D-glucose described in Example I. Interesterification of the ethyl lactoside heptaacetate with methyl oleate is conducted according to the method of Example V yielding ethyl lactoside polyoleate. Similarly, interesterification of ethyl glucoside tetraacetate and ethyl galactoside tetraacetate (see Example II) with methyl oleate according to the method of Example V yields ethyl glucoside tetraoleate and ethyl galactoside tetraoleate respectively.

Deep Fat Frying

EXAMPLE XII

Low calorie potato chips are produced by frying thin potato slices in ethyl lactoside polyoleate. For each chip a 5 g aliquot of ethyl lactoside polyoleate is poured into a small glass cooking vessel and heated to approximately 360° F. Small potato slices having a thickness of 2 to 3 mm and a diameter of 2 to 3 cm are added to the oil and fried until done.

EXAMPLE XIII

Low calorie potato chips are produced by the method of Example XII by substituting ethyl glucoside tetraester for the ethyl lactoside polyoleate. The ethyl glucoside tetraester is produced by reacting ethyl glucoside tetraacetate, ethyl myristate and ethyl oleate in a ratio of 1:2:6 according to the method of Example V.

EXAMPLE XIV

Low calorie potato chips are produced by frying thin potato slices in ethyl glucoside fatty acid polyester frying oil. For each potato chip, a 4 g aliquot of ethyl glucoside tetraoleate is combined with a 1 g aliquot of ethyl glucoside tetrapalmitate and the resulting mixture is poured into a small glass cooking vessel and heated to approximately 360° F. Small potato slices, having a thickness of 2 to 3 mm and a diameter of 2 to 3 cm are added to the oil and fried until done. Low calorie potato chips produced in this way have satisfactory taste and texture.

EXAMPLE XV

The procedure described in Example XIV is employed to produce low calorie potato chips by substituting the same quantity of ethyl galactoside fatty acid polyester of peanut oil FAEE for ethyl glucoside tetraoleate in the frying oil.

EXAMPLE XVI

The procedure described in Example Xiv is employed to produce low calorie potato chips by substituting the same quantity of ethyl lactoside heptastearate for ethyl glucoside tetrapalmitate in the frying oil. These low calorie potato chips have satisfactory texture and flavor.

EXAMPLE XVII

The procedure described in Example XIV is employed to produce low calorie potato chips by substituting the same quantity of sucrose octapalmitate for the ethyl glucoside tetrapalmitate.

EXAMPLE XVIII

The procedure described in Example XIV is employed to produce low calorie potato chips by substituting the same quantity of tripalmitin for the ethyl glucoside tetrapalmitate.

EXAMPLE XIX

The procedure described in Example XIV is employed to produce satisfactory low calorie potato chips by substituting the same quantity of ethyl glucoside fatty acid polyester of peanut oil FAEE for ethyl glucoside tetraoleate in the frying oil.

EXAMPLE XX

The procedure described in Example XIV is employed to produce satisfactory low calorie potato chips by substituting the same quantity of ethyl 4'-galactosyl lactoside fatty acid polyester for ethyl glucoside tetraoleate in the frying oil.

Spoonable White Salad Dressing

EXAMPLE XXI

A low calorie spoonable white salad dressing is prepared by replacing the oil in a typical recipe of this type with ethyl 4'-galactosyl lactose fatty acid polyester prepared from safflower oil FAEE. Mixing the ingredients in the proportions below produced a salad dressing with satisfactory consistency and taste.

| Ingredient | Percent by weight |
|---|---|
| Ethyl 4'-galactosyl lactose fatty acid polyester | 30.0 |
| Starch paste | 60.0 |
| starch | |
| sugar | |
| salt | |
| vinegar | |
| water | |
| Egg yolk | 5.0 |
| Water | 3.9 |
| Vinegar | 1.0 |
| Gum | 0.1 |
| | 100.0 |

Similar results are obtained when the 30% Ethyl 4'-galactosyl lactose fatty acid polyester is substituted with 4% ethyl glucoside tetraoleate and 26% safflower oil.

EXAMPLE XXII

A low calorie spoonable white salad dressing is prepared by replacing the oil in a typical recipe of this type with ethyl glucoside polyesters. Mixing the ingredients in the proportions below produced a salad dressing with satisfactory consistency and taste.

| Ingredient | Percent by Weight |
|---|---|
| Ethyl glucoside tetraoleate | 20.0 |
| Ethyl glucoside tetrapalmitate | 10.0 |
| Starch paste | 60.0 |
| starch | |
| sugar | |
| salt | |
| vinegar | |
| water | |
| Egg yolk | 5.0 |
| Water | 3.9 |
| Vinegar | 1.0 |
| Gum | .1 |
| | 100.0 |

Similar results are obtained when sucrose octapalmitate is substituted for the ethyl glucoside tetrapalmitate.

EXAMPLE XXIII

The ingredients in Example XXII are employed to produce a satisfactory low calorie spoonable white salad dressing by substituting the same quantity of ethyl glucoside fatty acid polyester of peanut oil FAME for ethyl glucoside tetraoleate in the oil.

EXAMPLE XXIV

The ingredients in Example XXII are employed to produce a satisfactory low calorie spoonable white salad dressing by substituting the same quantity of ethyl galactoside tetrastearate for ethyl glucoside tetrapalmitate in the oil.

EXAMPLE XXV

The ingredients in Example XXII are employed to produce a satisfactory low calorie spoonable white salad dressing by substituting the same quantity of ethyl 4'-galactosyl lactoside fatty acid polyester for ethyl glucoside tetraoleate in the oil.

Italian Salad Dressing

EXAMPLE XXVII

A low calorie Italian salad dressing is prepared by substituting the oil found in typical recipes of this type with ethyl 4'-galactosyl lactose fatty acid polyester prepared from safflower FAEE as described in Example VII.

| Ingredient | Percent by Weight |
|---|---|
| Ethyl 4'-galactosyl lactose fatty acid polyester | 40.00 |
| Water | 35.45 |
| Lemon juice | 5.80 |
| Vinegar (120 grain) | 13.00 |
| Salt | 3.50 |
| Starch | 0.80 |
| Garlic | 2.00 |
| Onion and garlic | 1.00 |
| Other spices | 0.25 |
| | 100.00 |

Similar results are obtained by substituting 20% safflower oil, 10% ethyl glucoside tetraoleate, and 10% ethyl glucoside tetramyristate for the ethyl 4'-galactosyl lactose polyester.

EXAMPLE XXVIII

Low calorie salad dressing is produced by substituting the same percent by weight of ethyl lactoside fatty acid polyester prepared as described in Example IX for the ethyl 4'-galactosyl lactose fatty acid polyester in the salad dressing recipe of Example XXVII.

EXAMPLE XXIX

A low calorie Italian salad dressing is prepared by substituting the triglyceride oil found in typical recipes of this type with ethyl lactoside polyester prepared from safflower FAME as described in Example VIII, and the glycoside AAL agent ethyl lactoside heptastearate.

| Ingredient | Percent by Weight |
|---|---|
| Ethyl lactoside from safflower FAME | 30.00 |
| Ethyl lactoside heptastearate | 10.00 |
| Water | 35.45 |
| Lemon juice | 5.80 |
| Vinegar (120 grain) | 13.00 |
| Salt | 3.50 |
| Starch | .80 |
| Garlic | 2.00 |
| Onion and garlic | 1.00 |

-continued

| Ingredient | Percent by Weight |
|---|---|
| Other spices | .25 |
| | 100.00 |

EXAMPLE XXVII

Low calorie salad dressing is produced by substituting the same percent by weight of ethyl galactoside tetraoleate prepared as described above for the ethyl glucoside tetraoleate in the salad dressing recipe of Example XXIII.

All of the alkyl glycoside fatty acid polyesters produced in accordance with the present invention are usable as substitutes for naturally occurring fats and oils. The process for producing low calorie foods and the novel products produced, have been described in conjunction with preferred embodiments. One of ordinary skill, after reviewing the foregoing specification, will be able to make various changes, substitutions of equivalents, and other alterations without departing from the broad concepts disclosed herein. It is therefore intended that protection afforded by Letters Patent hereon be limited only by the definition contained in the appended claims and equivalents thereof.

While the preferred embodiment of the invention has been described, other modifications may be made thereto and other embodiments may be devised within the spirit of the invention and scope of the appended claims.

What is claimed is:

1. In a process for producing a low calorie food containing fat ingredients and nonfat ingredients including the step of substituting a fat substitute for the fat ingredients, the improvement comprising selecting a fat substitute that comprises greater than 10% of an alkyl glycoside fatty acid polyester, the alkyl glycoside fatty acid polyester having at least 4 fatty acid ester groups, wherein each fatty acid independently has from 4 to 24 carbons atoms, and wherein the alkyl glycoside moiety comprises a saccharide portion and an alkyl portion, the alkyl portion having from 1 to 24 carbon atoms.

2. The process of claim 1, wherein the fatty acids are selected from the group consisting of saturated fatty acids, unsaturated fatty acids, and mixtures thereof.

3. The process of claim 1, wherein the saccharide portion is selected from the group consisting of fructose, glucose, galactose, mannose, ribulose, rhaminose, xylose, xylulose, ribose, arabinose, sorbose, maltose, lactose, cellobiose, melibiose, and 4'-galactosyl lactose.

4. The process of claim 1, wherein the alkyl portion is selected from the group consisting of methyl, ethyl, n-propyl, n-butyl, n-pentyl, n-octyl, n-decyl, n-dodecyl, n-tetradecyl, n-hexadecyl, n-octadecyl and structural isomers thereof.

5. The process of claim 1, wherein the fat substitute comprises a mixture of alkyl glycoside fatty acid polyesters.

6. The process of claim 5, wherein the fatty acids of alkyl glycoside fatty acid polyester are selected from the group consisting of saturated fatty acids, unsaturated fatty acids, and mixtures thereof.

7. The process of claim 1, wherein the fat substitute further comprises an effective amount of an anti-anal leakage agent to prevent anal leakage.

8. In a process for producing a low calorie food containing fat ingredients and nonfat ingredients including the step of substituting a fat substitute for the fat ingredients, the improvement comprising selecting a fat substitute that comprises an alkyl glycoside fatty acid polyester, the alkyl glycoside fatty acid polyester having at least 4 fatty acid ester groups, the fatty acid ester groups being selected from the group consisting of unsaturated fatty acids, and mixtures of saturated and unsaturated fatty acids, wherein each fatty acid independently has from 4 to 24 carbon atoms, and wherein the alkyl glycoside moiety comprises a saccharide portion and an alkyl portion, the alkyl portion having from 1 to 24 carbon atoms.

9. The process of claim 8, wherein the saccharide portion is selected from the group consisting of fructose, glucose, galactose, mannose, ribulose, rhaminose, xylose, xylulose, ribose, arabinose, sorbose, maltose, lactose, cellobiose, melibose, and 4'-galactosyl lactose.

10. The process of claim 8, wherein the alkyl portion is selected from the group consisting of methyl, ethyl, n-propyl, n-butyl, n-pentyl, n-octyl, n-decyl, n-dodecyl, n-tetradecyl, n-hexadecyl, n-octadecyl and structural isomers thereof.

11. The process of claim 8, wherein the fat substitute comprises a mixture of alkyl glycoside fatty acid polyesters.

12. The process of claim 8, wherein the fat substitute further comprises an effective amount of an anti-anal leakage agent to prevent anal leakage.

13. In a process for producing a low calorie food containing fat ingredients and nonfat ingredients including the step of substituting a fat substitute for the fat ingredients, the improvement comprising selecting a fat substitute that comprises a mixture of alkyl glycoside fatty acid polyesters, each alkyl glycoside fatty acid polyester having at least 4 fatty acid ester groups, wherein each fatty acid independently has from 4 to 24 carbon atoms, and wherein the alkyl glycoside moiety comprises a saccharide portion and an alkyl portion, the alkyl portion having from 1 to 24 carbon atoms, the mixture comprising alkyl glycoside fatty acid polyesters in which the fatty acids are selected from the group consisting of unsaturated fatty acids, and saturated and unsaturated fatty acids.

14. The process of claim 13, wherein the saccharide portion is selected from the group consisting of fructose, glucose, galactose, mannose, ribulose, rhaminose, xylose, xylulose, ribose, arabinose, sorbose, maltose, lactose, cellobiose, melibiose, and 4'-galactosyl lactose.

15. The process of claim 13, wherein the alkyl portion is selected from the group consisting of methyl, ethyl, n-propyl, n-butyl, n-pentyl, n-octyl, n-decyl, n-dodecyl, n-tetradecyl, n-hexadecyl, n-octadecyl and structural isomers thereof.

16. The process of claim 13, wherein the mixture further comprises an effective amount of an anti-anal leakage to prevent anal leakage.

17. In a process for producing a low calorie food including the step of contacting the food with a fat substitute the improvement comprising selecting a fat substitute that comprises greater than 10% of an alkyl glycoside fatty acid polyester, the alkyl glycoside fatty acid polyester having at least 4 fatty acid ester groups, wherein each fatty acid independently has from 4 to 24 carbon atoms, and wherein the alkyl glycoside moiety comprises a saccharide portion and an alkyl portion, the alkyl portion having from 1 to 24 carbon atoms.

18. The process of claim 17, wherein the fatty acids are selected from the group consisting of saturated fatty acids, unsaturated fatty acids, and mixtures thereof.

19. The process of claim 17, wherein the saccharide portion is selected from the group consisting of fructose, glucose, galactose, mannose, ribulose, rhaminose, xylose, xylulose, ribose, arabinose, sorbose, maltose, lactose, cellobiose, melibiose, and 4'-galactosyl lactose.

20. The process of claim 17, wherein the alkyl portion is selected from the group consisting of methyl, ethyl, n-propyl, n-butyl, n-pentyl, n-octyl, n-decyl, n-dodecyl, n-tetradecyl, n-hexadecyl, n-octadecyl and structural isomers thereof.

21. The process of claim 17, wherein the fat substitute comprises a mixture of said alkyl glycoside fatty acid polyesters.

22. The process of claim 21, wherein the fatty acids of alkyl glycoside fatty acid polyester are selected from the group consisting of saturated fatty acids, unsaturated fatty acids, and mixtures thereof.

23. The process of claim 17, wherein the fat substitute further comprises an effective amount of an anti-anal leakage agent to prevent anal leakage.

24. In a process for producing a low calorie fried food product including the steps of heating a fat substitute and contacting a food with the heated fat substitute to produce the low calorie fried food product, the improvement comprising selecting a fat substitute that comprises an alkyl glycoside fatty acid polyester, the alkyl glycoside fatty acid polyester having at least 4 fatty acid ester groups, wherein each fatty acid independently has from 4 to 24 carbon atoms, and wherein the alkyl glycoside moiety comprises a saccharide portion and an alkyl portion, the alkyl portion having from 1 to 24 carbon atoms.

25. The process of claim 24, wherein the fatty acids are selected from the group consisting of unsaturated fatty acids, saturated fatty acids and mixtures thereof.

26. The process of claim 24, wherein the saccharide portion is selected from the group consisting of fructose, glucose, galactose, mannose, ribulose, rhaminose, xylose, xylulose, ribose, arabinose, sorbose, maltose, lactose, cellobiose, melibiose, and 4'-galactosyl lactose.

27. The process of claim 24, wherein the alkyl portion is selected from the group consisting of methyl, ethyl, n-propyl, n-butyl, n-pentyl, n-octyl, n-decyl, n-dodecyl, n-tetradecyl, n-hexadecyl, n-octadecyl and structural isomers thereof.

28. The process of claim 24, wherein the fat substitute comprises a mixture of said alkyl glycoside fatty acid polyesters.

29. The process of claim 28, wherein the fatty acids of each alkyl glycoside fatty acid polyester are fatty acids selected from the group consisting of saturated fatty acids, unsaturated fatty acids, and mixtures thereof.

30. The process of claim 24, wherein the fat substitute further comprises an effective amount of an anti-anal leakage agent to prevent anal leakage.

* * * * *